United States Patent [19]

Walker et al.

[11] Patent Number: 5,755,801
[45] Date of Patent: May 26, 1998

[54] PROSTHESES FOR KNEE REPLACEMENT

[76] Inventors: Peter Stanley Walker, 13 Pembroke Road, Moor Park, Middlesex HA6 2HP, England; John Nevil Insall, 170 E. End Ave., New York, N.Y. 10128

[21] Appl. No.: 276,850

[22] Filed: Jul. 18, 1994

[30] Foreign Application Priority Data

Jul. 16, 1993 [GB] United Kingdom ............ 9314832

[51] Int. Cl.⁶ .................................................. A61F 2/38
[52] U.S. Cl. .................................................. 623/20
[58] Field of Search ................................... 623/18, 20

[56] References Cited

U.S. PATENT DOCUMENTS

| | | | |
|---|---|---|---|
| 5,059,216 | 10/1991 | Winters | 623/20 |
| 5,071,438 | 12/1991 | Jones et al. | 623/20 |
| 5,192,328 | 3/1993 | Winters | 623/20 |
| 5,271,747 | 12/1993 | Wagner et al. | 623/20 |
| 5,330,533 | 7/1994 | Walker | 623/20 |
| 5,387,240 | 2/1995 | Pottenger et al. | 623/20 |
| 5,395,401 | 3/1995 | Bahler | 623/20 |

FOREIGN PATENT DOCUMENTS

| | | | |
|---|---|---|---|
| 551793 | 7/1993 | European Pat. Off. | 623/20 |
| 592750 | 4/1994 | European Pat. Off. | 623/20 |
| 2685632 | 7/1993 | France | 623/20 |
| 9322991 | 11/1993 | WIPO | 623/20 |
| WO 94/26212 | 11/1994 | WIPO . | |

*Primary Examiner*—Michael J. Milano
*Attorney, Agent, or Firm*—McDermott, Will & Emery

[57] ABSTRACT

A condylar replacement knee prosthesis has a tibial platform adapted for attachment to a resected tibia, a femoral component adapted for attachment to a resected femur and a plastics meniscal component interposed between the femoral and tibial components. The upper surface of the meniscal component is shaped to correspond with bearing surfaces of the femoral component. The meniscal component is guided for sliding movement in an anterior-posterior direction on the tibial component and for limited rotational movement, the rotational movement being centred about an axis which is displaced medially from the anterior-posterior centre line of the tibial component.

3 Claims, 4 Drawing Sheets

PROSTHESES FOR KNEE REPLACEMENT

TECHNICAL FIELD

BACKGROUND ART

This invention relates to prostheses for knee replacement, particularly those for total knee replacement operations.

Most of the knee replacement prostheses in common use are of the condylar replacement type where the arthritic joint surfaces are resected and replaced with cooperating metal and plastic surfaces. In designing a satisfactory prosthesis, the aim is to replicate as far as possible the natural movements of the knee. However, the knee is a complex joint and the transverse axis of pivoting moves backwards and forwards as the knee pivots. There is also a limited degree of axial rotation; such rotation being biassed to the medial side of the knee. One of the difficulties, however, in providing freedom of movement to allow such motion is to ensure, at the same time, that the artificial joint does not jam or dislocate in use.

DISCLOSURE OF THE INVENTION

The present invention provides a number of different approaches to the solution to the above problem. According to one aspect of the present invention, there is provided a prosthesis for knee replacement which comprises:

(a) a femoral component having at least one condylar bearing surfaces;

(b) a tibial component having a tibial platform;

(c) a meniscal component located between the condylar bearing surfaces and the tibial platform; and (d) guide means arranged to guide the meniscal component for movement in an arc about a medially displaced axis which extends substantially at right angles to the tibial plate and preferably lies outside the area of the tibial plate.

The prostheses of this invention are of the condylar replacement type. In prostheses of this type, some or all of the natural collateral and cruciate ligaments are retained to give stability to the artificial joint. Often, because of the difficulty in resecting the natural joint surfaces without damaging the cruciate ligaments, it is the practice to resect at least the posterior cruciate ligament. However, the collateral ligaments are generally retained.

Preferably, the guide means comprises a curved track which is upstanding on the tibial platform and cooperates with a recess in the meniscal component.

The tibial platform may include a stud extending upwardly from the tibial platform, which engages in a slot in the meniscal component. Preferably, such stud has a head which is larger than the cross section of the stud and engages in a corresponding groove in the meniscal component, thereby restraining lifting off of the meniscal component from the tibial platform.

According to a second embodiment of the present invention, there is provided a prosthesis for knee replacement which comprises:

(a) a femoral component having at least one condylar bearing surface;

(b) a tibial component having a tibial platform and an anterior-posterior centre line;

(c) a meniscal component located between the condylar bearing surface and the tibial platform;

(d) a stud upstanding from the platform and engaged in a recess in the meniscal component in such a way as to permit relative movement between the meniscal component and said stud and guide means, (normally remote from said stud and said recess), for guiding movement of the meniscal component relative to said platform in an arc which is centred on an axis which is substantially at right angles to the tibial platform, and is displaced medially from the anterior-posterior centre line of the platform.

As in the first embodiment of the invention, the stud is preferably provided with an enlarged head which engages in a groove in the meniscal component and restrains lifting off of the meniscal component from the platform.

Preferably, stops are provided to prevent the meniscal component sliding posteriorly or anteriorly beyond a predetermined sliding limit so as to reduce the risk of dislocation in use.

In one embodiment, the stud slides in a slot in the meniscal component which is closed at one or both ends to provide stops to prevent sliding movement of the meniscal component in the anterior-posterior direction beyond a predetermined limit. Where the slot is closed at both ends, the slot and rail would be designed as 'snap-on' engaging parts.

Guide means for guiding the meniscal component about an arc centred on a axis medially of the centre line of the tibial platform, are preferably formed by suitably engaging surfaces on the tibial platform and meniscal component. Preferably, such surfaces are curved and also include an upstanding curved surface on the tibial platform, engaging with the recess in the meniscal component. Preferably, the guidance is such that the axis about which the meniscal component rotates is centred at the edge of the tibial platform or beyond its physical extent.

Several embodiments of the present invention will now be described with reference to the accompanying drawings, in which:

DESCRIPTION OF THE INVENTION

Figure 1:
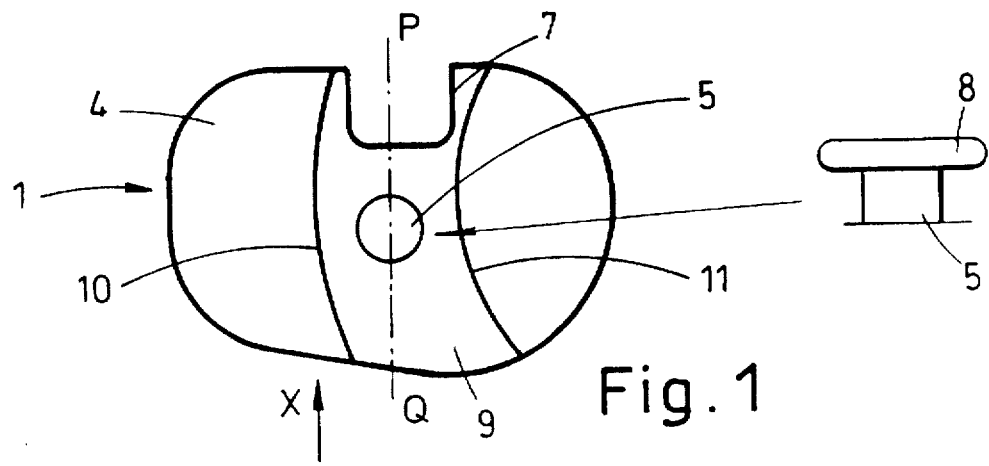
FIG. 1 is a plan view of a first embodiment of a tibial plate component in accordance with the invention.
Figure 1A:
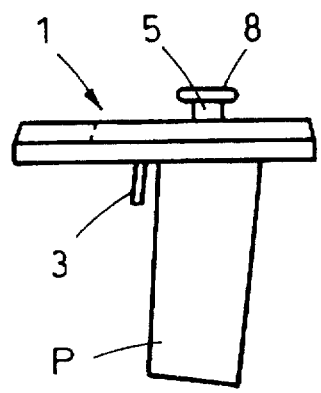
FIG. 1a is an elevational view in the anterior-posterior direction of the tibial plate shown in FIG. 1.
Figure 1B:
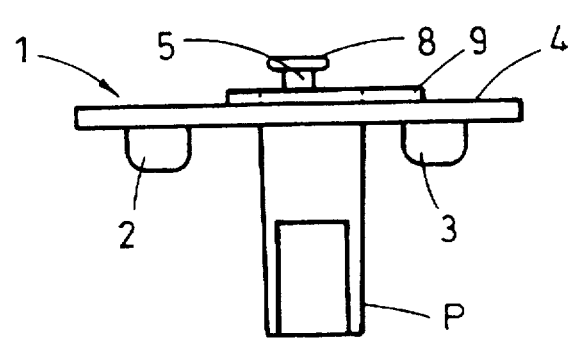
FIG. 1b is a view taken in the direction of the arrow X in FIG. 1a, FIG. 1c is a plan view of a meniscal component designed for use with the tibial platform shown in FIGS. 1 to 1b.
Figure 1C:
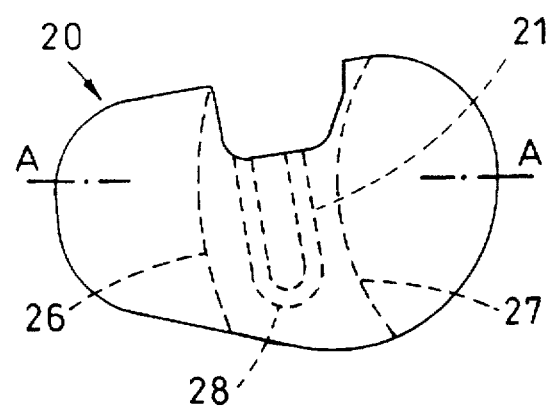
FIG. 1d is an elevational view of the meniscal component shown in FIG. 1c, taken in the anterior-posterior direction.
FIG. 1e is a sectional view on the line A—A in FIG. 1c.
Figure 1D:
Figure 1E:
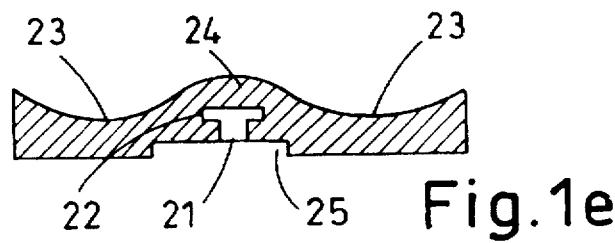

Referring to FIGS. 1 to 1e, the tibial component comprises a tibial platform 1, usually made from stainless steel or other non-corrosive metal and having downwardly extending projections 2 and 3 for engaging the platform in non-rotatable manner in the resected end of a tibia. The upper surface 4 of the platform has a flat horizontal surface with an upstanding stud 5 located on the centre line P-Q of the tibial component. The tibial platform is cut away at 7 at the posterior side of the platform to allow passage of the cruciate ligaments.

As can be seen best in FIG. 1a, the stud has a generally circular body and an enlarged head 8. Stud 5 extends upwardly from a raised portion 9 of the tibial base plate. The raised portion 9 forms a central upper platform which is bounded by curved sides 10 and 11. This central portion is typically about 2 to 3 mms higher than the general plane of the surface 4 of the tibial platform. A meniscal component 20 has a shape as seen in plan view which is similar to that of the tibial platform 1. However, it is slightly smaller in overall size than the platform on which it is mounted. The meniscal component 20 includes a slot 21 formed in the central area of the meniscal component. Slot 21 includes an enlarged groove 22, which is shaped to receive the stud and head 8 with some looseness between the stud and the recess to allow some freedom of motion.

As can be seen more clearly in FIG. 1d, the meniscal component is shaped with depressions 23 to receive the condylar bearing surfaces of the femoral part of the prosthesis. The meniscal component is thickened in the central part 24, so as to provide additional material for accommodating the slot and groove 21 and 22. The underside of the meniscal component is also recessed at 25 to provide a recess which extends from the anterior to the posterior side and has smoothly curved surfaces 26 and 27.

Surfaces 26 and 27 cooperate with curved edges 10 and 11 of the raised platform 9. The shape of the curves 26, 27 and 10, 11 are such that the centre of rotation of the meniscal component on the tibial platform lies outside the extent of the platform at a point indicated at A in FIG. 1c.

It will be noted that the slot 21 is open at the posterior end and closed at the anterior end 28. Because of the closed end 28, rotation of the meniscal component in the posterior direction is limited by the stud 5 reaching the end 28 of the slot 21. The open end of the slot enables the meniscal component to be assembled onto the stud 5 and, if desired, an additional abutment may be provided on the tibial platform to prevent excessive sliding movement of the meniscal component in the anterior direction.

The femoral component can be of the conventional type having a pair of condylar bearing surfaces. However, it is preferred to shape the condylar bearing surfaces and the upper surface of the meniscal component so as to be closely conforming, e.g. as described in our co-pending PCT Patent Application No. PCT/GB94/01047 filed on May 17, 1994 and designating USA or in U.S. patent application Ser. No. 08/163,623, filed on Dec. 9, 1993, the entire contents of both said applications are specifically incorporated herein.

Figure 2:
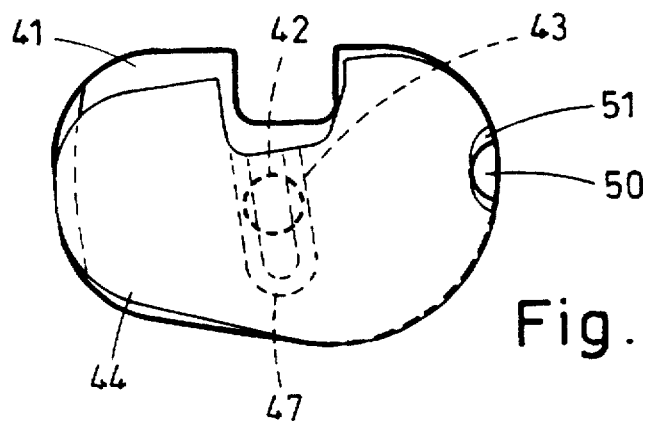
FIG. 2 is a plan view of a second embodiment of a tibial platform and meniscal component shown in the neutral or extended position of the knee.
Figure 2A:
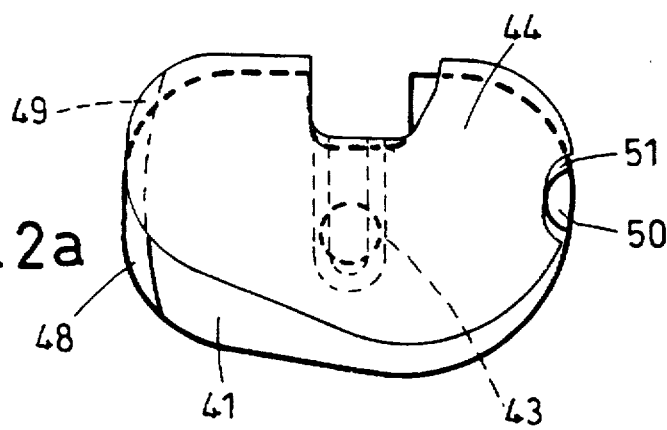
FIG. 2a shows the position with the plastic meniscal component rotated 10° externally on the tibial base plate.
Figure 2B:
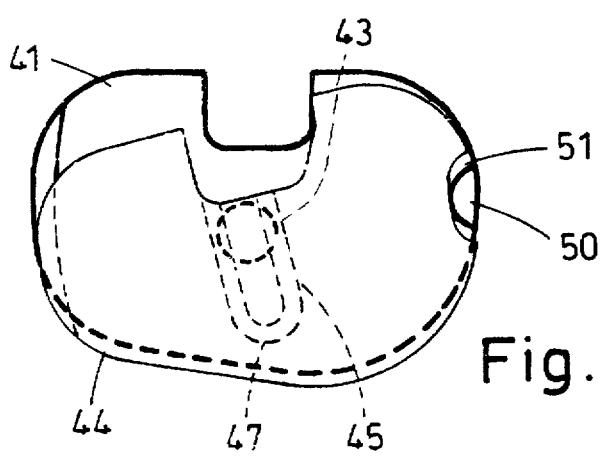
FIG. 2b shows the meniscal component rotated 5° internally on the tibial base plate.
Figure 2C:
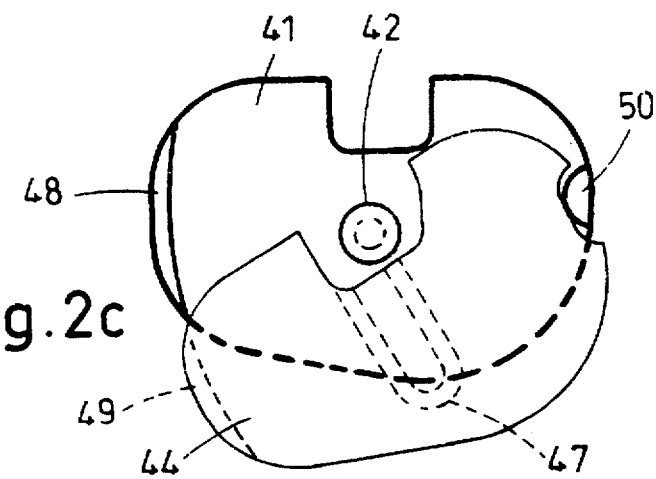
FIG. 2c shows the method of engaging the meniscal component on the tibial base plate.

A second embodiment in accordance with the invention is shown in FIGS. 2 to 2c. This embodiment has a number of similarities with that shown in FIGS. 1 to 1e and only the differences will be described.

In common with the FIG. 1 embodiment, the embodiment of FIG. 2 comprises a tibial platform 41 having means similar to those shown in FIG. 1 for attachment in non-rotational manner to a resected tibia. The upper surface of platform 41 is substantially flat except for an upstanding stud 42 which has an enlarged head similar to that shown in FIG. 1a. Stud 42 is received in a slot 43 in the meniscal component 44 and slot 43 includes an upper groove 45 for receiving the head of the stud 42 in such a way as to prevent lift-off of the meniscal component from the platform. Slot 43 is closed at the anterior end 47 in order to provide a stop for movement of the meniscal component in the posterior direction. A stop or brake for movement in the opposite direction is provided by a rail 48 which engages in a corresponding recess 49 of the meniscal component.

Rotation of the meniscal component 44 about an axis X at the edge of the tibial platform is controlled by a semi-circular abutment 50 which is upstanding at the medial side of the platform. A recess or notch 51 is formed in the corresponding portion of the meniscal component and is rounded as shown to allow approximately 2 mms movement in an anterior and posterior direction.

FIG. 2c shows the manner in which the meniscal component can be fitted to the tibial platform by engaging the abutment 50 in the recess 51 and then the stud 42 in its corresponding slot 43.

FIGS. 2a and 2b show different relative positions of the meniscal component on the tibial platform at different degrees of internal and external rotation.

Referring to FIGS. 3, 3a, 3b and 3c, in this embodiment sliding movement of the meniscal component 101 in the tibial platform 102 is guided by a curved rail 103 which is upstanding from the platform. Preferably, the rail is 'T'-shaped in section and the corresponding groove 105 in the meniscal component is similarly shaped. Consequently, a section on the line A—A in FIG. 3 will be similar to the sectional view of FIG. 1e.

Figure 3:
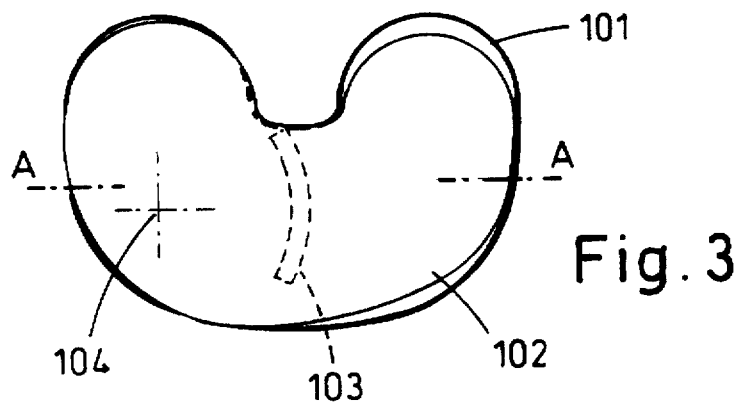
FIG. 3 is a plan view of a further embodiment showing a tibial platform with a meniscal component in place on the platform. The meniscal component is shown as transparent, although normally it would be opaque or translucent.
Figure 3A:
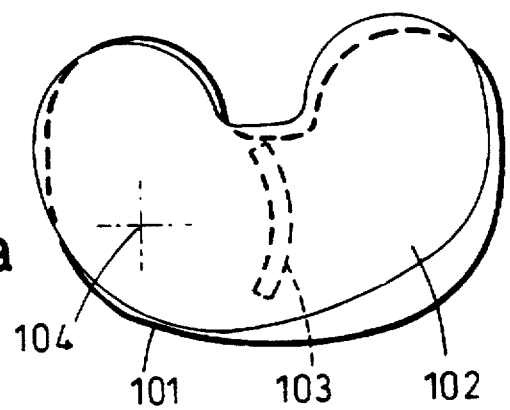
FIGS. 3a and 3b show the meniscal component at different degrees of rotation on the platform.
Figure 3B:
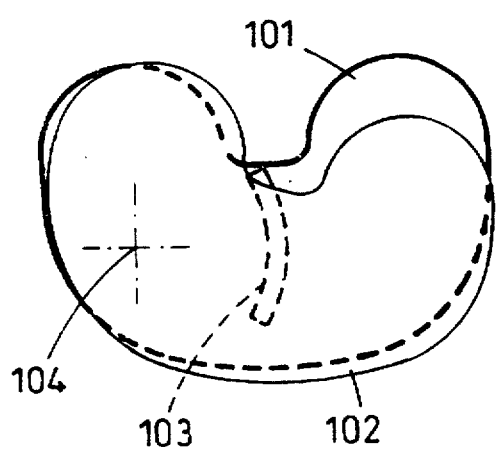
Figure 3C:
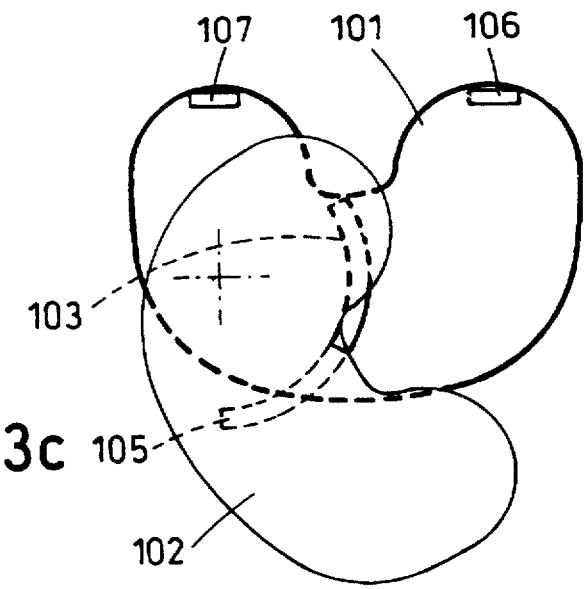
FIG. 3c shows one method of installing the meniscal component on the curved rail.

As shown in FIG. 3a, the rotation of the meniscal component 102 on the tibial platform is centred on a medially displaced axis 104. The method of assembling the meniscal component on the platform is shown in FIG. 3c.

Preferably, stops are provided to limit the extent of rotational movement. For example, the curved slot may be closed at one end or a stop or stops 106, 107 may extend upwardly from the platform 101.

In common with the arrangement shown in FIG. 1, the embodiments of FIGS. 2 and 3 is preferably used with a closely conforming femoral component and meniscal component. The design shown in the above cited European and PCT applications are preferred.

Referring to FIGS. 4a, 4b, 4c and 4d, these Figures show details of the femoral component and the manner in which the femoral component interacts with the meniscal component in a prosthesis having closely conforming femoral and meniscal components. These Figures do not show the way in which the meniscal component is guided on the tibial platform since these features are shown in the other Figures.

Figure 4A:
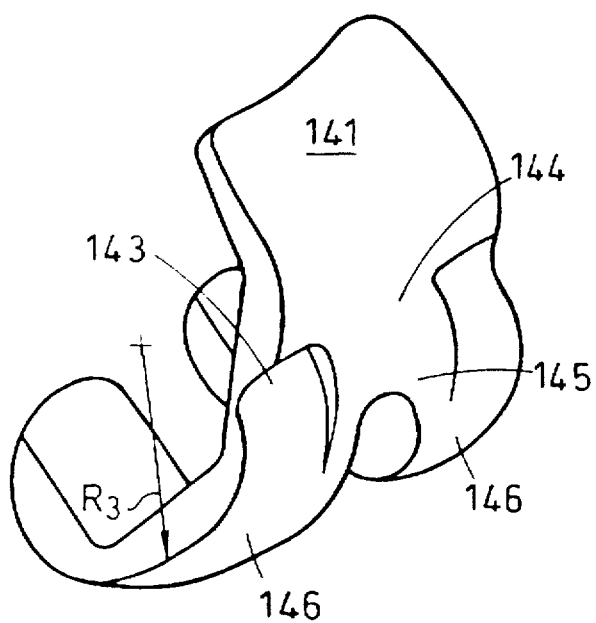
FIG. 4a is a perspective view of a femoral component.

Referring to FIG. 4a, it will be seen that the femoral component 141 is a one-piece construction in that the condyles 146 are formed integrally with the patella bearing surface 144. The condyles 146 of the femoral component have a radius $R_3$ which substantially corresponds to the radius $R_4$ of the tibial bearing surfaces 147 of the meniscal component 142. The radius $R_3$ is continued anteriorly, as shown, so as to cut away material in the condylar regions at 143, while leaving the patella bearing surface 144 unaffected. The central region 145 of the meniscal component 142 is shallower than the tibial surfaces 147 to provide clearance for the patella surface anteriorly and to prevent impingement in further flexion posteriorly. Because the patella bearing surface 144 is unaffected by the cutting away of the condylar surfaces anteriorly at 143, the lever arm of the patella is not shortened as in the case of the prior art arrangements. Because of the close conformity between the condylar portions and the corresponding bearing surfaces of the meniscal component, there is uniform spreading of the load transmitted through the femoral components over a large surface of the meniscal component and without loss of the patella lever arm. The cut out regions of the condylar parts of the femoral component do not require additional resection, since they are cut away only in the material of the prosthesis. The required laxity in the joint is provided by mounting the meniscal component 142 for guided sliding and rotational movement on a tibial base plate 150 as shown in FIGS. 1 to 3. The tibial base plate is attached in conventional manner, e.g. by a post P and locating pins 2 and 3 (see FIG. 1b) to the resected tibia 148.

Figure 4C:
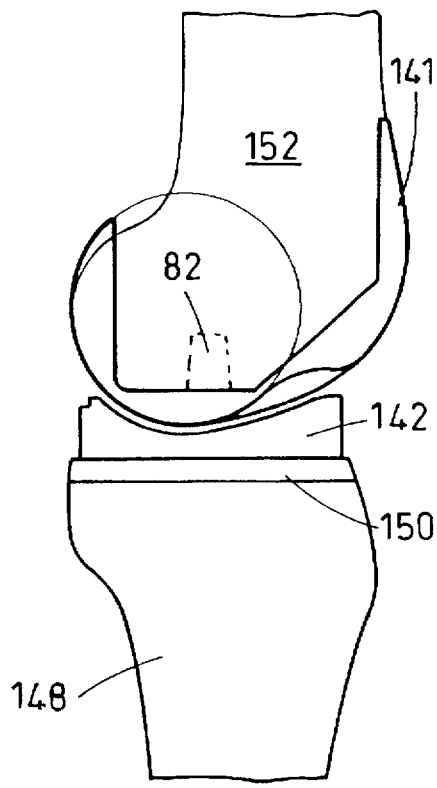
FIG. 4c is an elevation showing the relationship between the femoral, meniscal and tibial components.
Figure 4B:
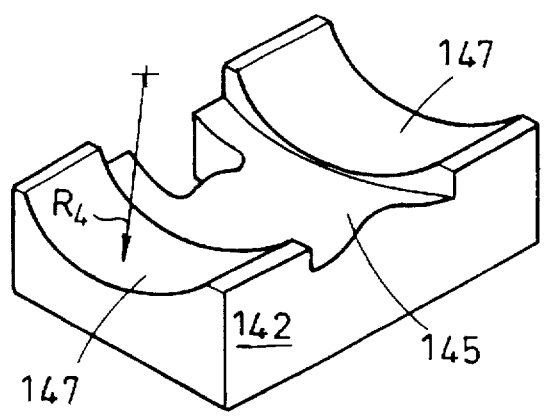
FIG. 4b is a perspective view of a meniscal component showing the condylar bearing surfaces but omitting the parts which engage with the tibial platform.
Figure 4D:
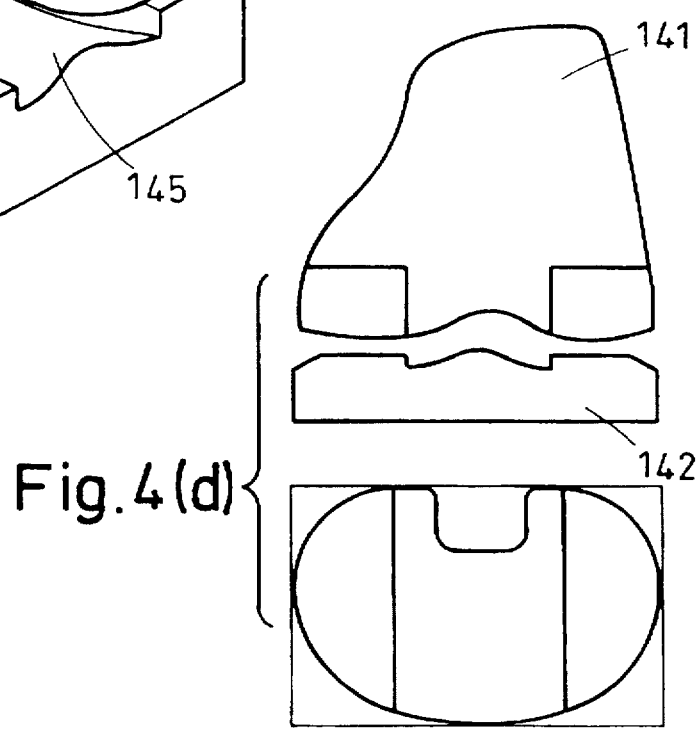
FIG. 4d shows anterior and plan views of the femoral and meniscal components.

As shown in FIG. 4c, the femoral component 141 is fixed to the femur 152 after resecting the natural condyles and fixed with studs 82 extending upwardly from each condylar portion 146. The construction of the femoral component and the bearing surfaces on the upper surface of the meniscal component is described in more detail in our pending patent application PCT/GB94/01047, filed May 17th 1994. The entire PCT/GB94/01047 application is incorporated herein by reference.

In all the embodiments, the meniscal component is assymetric about the centre line P-Q. This ensures that when the meniscal component rotates about a medially displaced axis, any ligaments which extend through the posterior cut-away portion in the tibial base plate are not trapped between the meniscal component and the base plate.

In the construction described above the femoral components and tibial metal platform are made from a metal acceptable for use for implantation in the human body. Examples are cobalt-chromium and titanium alloys and stainless steels. The artificial patella (where present) and/or the plastics bearing components may be made from any biocompatible material capable of withstanding the imposed loads and providing appropriate bearing properties when in contact with a polished metal surface. Preferably, the plastics material should exhibit low friction properties under these conditions. Examples of suitable materials are ultra-high molecular weight polyethylene or acetal copolymers.

We claim:

1. A prosthesis for knee replacement which comprises:
   (a) a femoral component having at least one condylar bearing surface;
   (b) a tibial component comprising a substantially planar tibial platform having an anterior-posterior axis;
   (c) a meniscal component located between the condylar bearing surface and the tibial platform;
   (d) a stud upstanding from the platform and engaged in a recess slot in the meniscal component to permit relative rotational movement of the component about the stud and sliding movement of the meniscal component on the tibial platform in an anterior-posterior direction, the slot being closed at least at one end, thereby providing a stop limiting the extent of anterior-posterior sliding movement of the meniscal component on the tibial platform; and,
   (e) an abutment upstanding at one edge of the tibial platform which engages with a recess in one edge of the meniscal component, thereby guiding and limiting movement of the meniscal component in an arc around the abutment.

2. A prosthesis as claimed in claim 1 wherein the recess slot in the meniscal component which receives the stud is a slot which extends in the direction of the anterior-posterior axis.

3. A prosthesis as claimed in claim 1 wherein the recess slot in the meniscal component which receives the stud is a slot which extends at an acute angle to the direction of the anterior-posterior axis.

* * * * *